(12) United States Patent
Karim et al.

(10) Patent No.: US 6,624,211 B2
(45) Date of Patent: Sep. 23, 2003

(54) DENTAL MATERIALS WITH EXTENDABLE WORK TIME, KITS, AND METHODS

(75) Inventors: Naimul Karim, Maplewood, MN (US); Joel D. Oxman, St. Louis Park, MN (US); Ahmed S. Abuelyaman, Woodbury, MN (US); Babu N. Gaddam, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/858,752

(22) Filed: May 16, 2001

(65) Prior Publication Data

US 2002/0115743 A1 Aug. 22, 2002

Related U.S. Application Data

(63) Continuation-in-part of application No. 09/541,417, filed on Apr. 3, 2000, now abandoned.

(51) Int. Cl.$^7$ ................................ A61K 6/03
(52) U.S. Cl. .................. 523/116; 523/115; 523/117; 522/47; 522/48; 522/51; 522/57; 522/60; 522/61; 522/64; 522/65; 522/908; 433/228.1
(58) Field of Search ................... 523/105, 109, 523/115, 116, 117; 433/228.1; 106/35; 522/47, 48, 51, 57, 60, 61, 64, 65, 908

(56) References Cited

U.S. PATENT DOCUMENTS

| | | |
|---|---|---|
| 3,740,850 A | 6/1973 | Bowen et al. |
| 3,928,280 A | 12/1975 | Erickson et al. |
| 4,071,424 A | 1/1978 | Dart et al. |
| 4,221,698 A | 9/1980 | Lee, Jr. et al. |
| 4,243,763 A | 1/1981 | Argentar et al |
| 4,284,551 A | 8/1981 | Argentar |
| 4,503,169 A | 3/1985 | Randklev |
| 4,536,523 A | 8/1985 | Antonucci |
| 4,538,920 A | 9/1985 | Drake |
| 4,628,112 A | 12/1986 | Winkel et al. |
| 4,642,126 A | 2/1987 | Zador et al. |
| 4,652,274 A | 3/1987 | Boettcher et al. |
| 4,673,713 A | 6/1987 | Meier et al. |
| 4,695,251 A | 9/1987 | Randklev |
| 4,772,530 A | 9/1988 | Gottschalk et al. |
| 4,774,267 A | 9/1988 | Weintraub |
| 4,874,450 A | 10/1989 | Gottschalk |
| 4,954,414 A | 9/1990 | Adair et al. |
| 5,055,372 A | 10/1991 | Shanklin et al. |
| 5,057,393 A | 10/1991 | Shanklin et al. |
| 5,320,886 A | 6/1994 | Bowen |
| 5,426,134 A | 6/1995 | Rheinberger et al. |
| 5,525,647 A | 6/1996 | Eichmiller |
| 5,545,676 A | 8/1996 | Palazzotto et al. |
| 5,583,164 A | 12/1996 | Jochum et al. |
| 5,643,994 A | * 7/1997 | Kish et al. |
| 5,698,611 A | 12/1997 | Okada et al. |
| 5,908,879 A | 6/1999 | Kawashima et al. |
| 6,191,191 B1 | 2/2001 | Harada et al. |

FOREIGN PATENT DOCUMENTS

| | | |
|---|---|---|
| EP | 0 173 567 A2 | 3/1986 |
| EP | 0 176 777 A | 4/1986 |
| GB | 714868 | 9/1954 |
| JP | 77623 * | 3/1997 |
| JP | 9-77623 A | 3/1997 |
| JP | 9-77623 | 3/1997 |
| WO | WO 95/30480 | 11/1995 |
| WO | WO 96/30480 | 11/1995 |
| WO | WO 97/35916 | 10/1997 |
| WO | WO 99/40884 | 8/1999 |

OTHER PUBLICATIONS

Kirk–Othmer, *Encyclopedia of Chemical Technology*, "Peroxides and Peroxy Compounds, Inorganic," 3$^{rd}$ Ed., vol. 17, pp. 1–4, 6, 9, 11, 19–23, 27–55, 60–63, 73, 83–86.
American National Standard Institute/American Dental Association Specification No. 27, "Resin–Based Filling Materials," Council on Dental Materials, Instruments and Equipment, Chicago, IL, pp. 1–36 (Jul. 16, 1993).
ASTM Designation: D–2240–97, "Standard Test Method for Rubber Property–Durometer Hardness," *Annual Book of ASTM Standards*, pp. 388–391 (1997).
*Restorative Dental Materials*, "Prosthetic Applications of Polymers," pp. 541–542.
*Revised American National Standard/American Dental Association Specification No. 9*, "For Dental Silicate Cement," Council on Dental Materials, Instruments and Equipment, 17 pages (Jun. 30, 1980).
Materials from web site <http://www.dentaldigest.com/scripts/results/cfm.> Aug. 27, 1999.

* cited by examiner

Primary Examiner—Peter Szekely
(74) Attorney, Agent, or Firm—Doreen S. L. Gwin

(57) ABSTRACT

The present invention provides a dental material that includes a hardenable resin system and a first initiator system capable of hardening the hardenable resin.

27 Claims, 1 Drawing Sheet

DENTAL MATERIALS WITH EXTENDABLE WORK TIME, KITS, AND METHODS

RELATED APPLICATIONS

This application is a continuation-in-part of U.S. Pat. application Ser. No. 09/541,417, filed on Apr. 3, 2000, now abandoned, which is hereby incorporated by reference in its entirety.

FIELD OF THE INVENTION

This invention relates to dental materials with an extendable work time. More specifically, the dental materials have a relatively fast initial set phase and a subsequent extended flexible phase working time. Preferably, the dental materials are used as provisional oral prosthetic devices such as inlays, onlays, veneers, temporary crowns, permanent crowns, and bridges.

BACKGROUND OF THE INVENTION

Currently available dental materials for the fabrication of provisional restoratives include polymerizable resins, which have replaced the use of metal shells and polycarbonate temporary crowns. Resin-based crowns can be made available in different shades that can be matched to the patient's dentition. Two-part resin formulations are typically used wherein the resin constituents are separate from the initiator system. The resin constituents are typically free radically polymerizable monomers (e.g., acrylates, methacrylates, and acrylamides). The initiator system typically includes reducing agents, such as tertiary amines, and oxidizing agents, such as peroxides, as accelerators or activators for free radical polymerization and control of the rate of polymerization.

It is desirable to control the rate of polymerization such that the dental material has a relatively rapid initial set phase time during which time a specific hardness is attained without locking into the undercuts produced during tooth preparation, followed by an extended flexible phase work time. During this flexible phase the dental material can be removed from the mouth to allow the dental practitioner time to modify, trim, and adjust the dental material for a custom fit onto the prepared tooth. Modification and adjustment of the dental material during the extended flexible phase is desirable in order to provide a more custom fit of the provisional restorative in the mouth of the patient. Additionally, heat generated by the exothermic polymerization is controlled by removal of the dental material from the intra-oral environment. This also avoids damage to oral tissues and consequently provides more comfort for the patient. Before final placement in the mouth and cementing in place, the restorative is completely hardened by conventional means commonly known for free radical polymerization.

A typical procedure for making a provisional dental restorative involves the following steps. Initially, an alginate impression is taken before preparing the teeth. The impression is rinsed, set aside, and wrapped in a moist paper towel. The teeth are then prepared and the correct shade of acrylic powder is selected to match the natural teeth. An acrylic liquid resin and the acrylic polymeric powder, one of which includes a reducing agent and the other of which includes an oxidizing agent, are mixed together and placed in the impression. The impression is placed aside until the composition thickens and forms a dull appearance (approximately 45–60 seconds). Meanwhile, the prepared teeth and surrounding tissue are coated with a petroleum jelly, which ensures easy removal of the acrylic temporary from the preparation and protects the teeth and tissue from irritation by the acrylic mixture. The impression with the acrylic mixture is seated in the mouth and held in place for a sufficient time to allow it to harden to a removable state. Mixing through this stage is the initial set phase time. The acrylic material is removed from the impression and gross excess acrylic is trimmed. The acrylic material is placed in and out of the mouth while the acrylic material is in a rubbery state. This is the extended flexible phase work time. The acrylic material is removed from the mouth and set aside until the acrylic is fully cured. The fit of the acrylic restorative is checked and adapted to fit, if necessary. Excess acrylic is trimmed with an acrylic bur or stone and polished to a smooth finish. The acrylic temporary is then cemented into place.

The important time during the preparation of a restorative occurs after the resin, initiator, and reducing agent are mixed together. It is important that hardening occurs initially rapidly (during the initial set phase time), but then slows to allow a dental practitioner to place, remove, and trim the restorative material (during the extended flexible phase work time) before it continues to harden to such a state as to become unworkable. There is a need for dental materials that provide reasonable initial set phase times and flexible phase work times that are more readily controllable than conventional materials.

SUMMARY OF THE INVENTION

The present invention provides a dental material useful for the fabrication of dental restoratives. Such a dental material includes a resin system and a first initiator system. Preferably, it also includes a filler system, and more preferably, a second initiator system. Once the components are combined to initiate a reaction, the time period during which the resultant composition solidifies to a partially hardened state is referred to herein as the initial set phase time. The partially hardened material at this point is firm enough to be removed from the mouth without being permanently deformed, but not so rigid that the solidified impression locks into undercuts and becomes too hard and brittle to be trimmed. The material then has an extended flexible phase work time sufficient for the dental practitioner to place, remove, and trim the dental material before it continues to harden to such a state as to become unworkable. The dental restorative can be further hardened to a rigid phase extra-orally.

In one embodiment, the dental material includes a hardenable resin system and a first initiator system capable of hardening the hardenable resin. Optionally and preferably, the dental material also includes a filler system and a second initiator system. Preferably, the hardenable resin system and the first initiator system are selected such that when combined the resultant composition has an initial set phase time of less than about 180 seconds at room temperature, and an extended flexible phase working time of greater than about 85 seconds at room temperature.

The first initiator system preferably includes at least one reducing agent and at least one oxidizing agent. Preferably, the oxidizing agent is a peroxide compound and the reducing agent is a tertiary aromatic amine, a mercaptan, or combinations thereof. Typically and preferably, the dental material is provided in at least two parts, wherein at least one part includes at least one reducing agent and at least one other part includes at least one oxidizing agent, which together form the first initiator system.

In a preferred embodiment, the dental material includes a hardenable resin system and a first initiator system capable of hardening the hardenable resin, wherein the first initiator system includes at least one polymerizable tertiary aromatic amine. Preferably, the polymerizable tertiary aromatic amine is selected from the group of bis-N,N-[2-(2-methacryloloxyethylaminocarbonyloxy)ethyl]-p-toluidine, bis-N,N-(2-methacryloloxyethyl)-p-toluidine, 4-[2(2-acrylamido-2-methylpropionyloxy)ethyl]-N,N-dimethlyaniline, bis-N,N-[2-(2-acrylamido-2-methylpropionyloxy)ethyl]-p-toluidine, and mixtures thereof.

In another preferred embodiment, the dental material includes a hardenable resin system and a first initiator system capable of hardening the hardenable resin, wherein the first initiator system includes at least two peroxide oxidizing agents.

In yet another preferred embodiment, the dental material includes a hardenable resin system and a first initiator system capable of hardening the hardenable resin, wherein the first initiator system includes at least two reducing agents, at least one of which is a mercaptan.

In still another preferred embodiment, the dental material is suitable for use as a provisional restorative and includes a hardenable resin system and a first initiator system capable of hardening the hardenable resin, wherein the first initiator system includes at least two tertiary aromatic amine reducing agents.

The present invention also provides a kit for preparation of a dental restorative. The kit includes: a first container including at least one reducing agent; a second container including at least one oxidizing agent; and at least a portion of a hardenable resin system in at least one of the containers; wherein the hardenable resin system, reducing agent, and oxidizing agent are selected such that when combined the resultant composition has an initial set phase time of less than about 180 seconds at room temperature, and an extended flexible phase working time of greater than about 85 seconds at room temperature.

In another embodiment, the kit includes: a first container including at least one oxidizing agent; a second container including at least one polymerizable tertiary aromatic amine reducing agent; and a hardenable resin system in at least one of the containers.

In yet another embodiment, the kit includes: a first container including at least two peroxide oxidizing agents; a second container including at least one reducing agent; and a hardenable resin system in at least one of the containers.

In still another embodiment, the kit includes: a first container including at least one oxidizing agent; a second container including at least two reducing agents, at least one of which is a mercaptan; and a hardenable resin system in at least one of the containers.

The present invention also provides a method for preparing a dental restorative. The method involves: making an impression of at least one tooth; filling the impression with a hardenable composition comprising a hardenable resin system and a first initiator system, wherein the hardenable resin system and the first initiator system are selected such that when combined the resultant composition has an initial set phase time of less than about 180 seconds at room temperature, and an extended flexible phase working time of greater than about 85 seconds at room temperature; placing the impression over at least one tooth to partially harden the hardenable composition; removing the impression and partially hardened composition and removing excess hardened material to form a dental restorative; and allowing the dental restorative to further harden.

DEFINITIONS

The dental materials of the present invention include a hardenable resin. As used herein, "harden," "hardening," and "hardenable" is descriptive of a resin that can be polymerized and/or crosslinked.

"Dental material" refers to a combination of components that upon reaction form a material that is suitable for use in a patient's dentition. Herein, dental material refers to the unreacted components (e.g., various combinations of hardenable resin, initiator systems, etc.) as well as the reacted components.

"Initial set phase time" is the time period, as measured in seconds, during which time the dental material hardens to a hardness of 20 (i.e., $T_{20}$), as determined by measuring with a Shore A Durometer (The Shore Instrument and Manufacturing Co., New York, N.Y.), at room temperature. Typically, the initial set phase time starts with mixing the oxidizing agent, reducing agent, and resin.

"Extended flexible phase time" is the time period wherein the dental material that has obtained a hardness of 20 on the Shore A Durometer is allowed to harden to a hardness of no greater than 80 (i.e., $T_{80}$), as determined by measuring with a Shore A Durometer, at room temperature. The extended flexible phase time, as measured in seconds, is obtained by subtracting $T_{20}$ from $T_{80}$.

"Restorative" refers to an oral prosthetic device, such as an inlay, onlay, a veneer, a single unit crown, a splint, a crown lining material for prefabricated crowns, an implant, or multiple unit bridges. "Provisional Restorative" is a temporary placement intended for eventual removal and replacement by a more long term or permanent device. Typically, a provisional restorative is intended to be in the intra-oral environment for no greater than about a year, preferably for no greater than about 6 months, and more preferably no greater than about 30 days.

DETAILED DESCRIPTION OF PREFERRED EMBODIMENTS OF THE INVENTION

Figure 1:
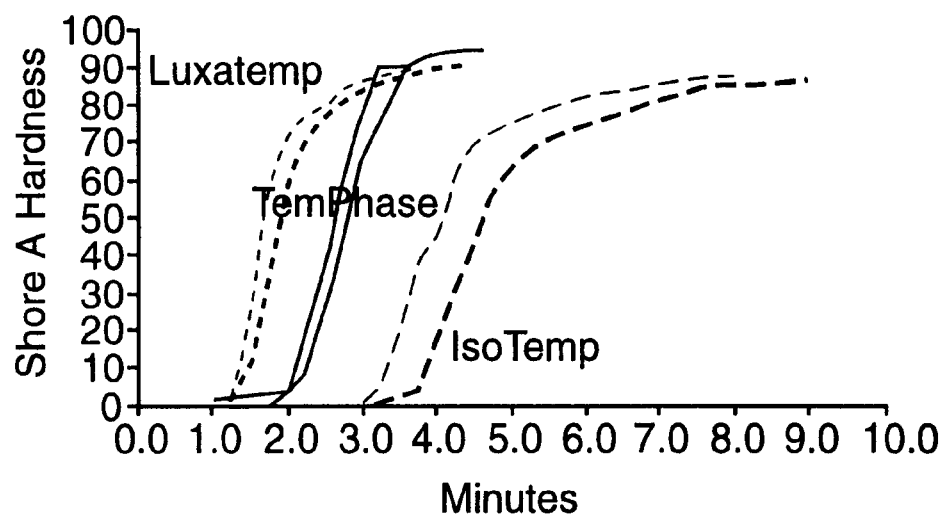
FIG. 1 is a chart of Shore A Hardness values of three comparative dental materials.

This invention addresses use of initiator systems and hardenable resins to design a dental material with a controllable initial set phase. The dental material is useful as a restorative, such as inlays, onlays, veneers, crowns, and bridges, for example. Preferably, the dental material is useful as a provisional restorative, such as a temporary crown and temporary bridge.

A dental material of the present invention includes a unique combination of a resin system and a first initiator system. Preferably, it also includes a filler system and a second initiator system. By judicious selection of these components, particularly the resin system and first initiator system, the dental material upon mixing of the components preferably exhibits an initial hardening to 20 on a Shore A Durometer in no greater than about 180 seconds (i.e., an initial set phase time). This initial hardening of the composition not only captures the topography of the prepared tooth, but also the composition is still easily removable from the mouth as a flexible or rubbery solid. Preferably, for at least about 85 seconds after removing the partially hardened dental material from the mouth the dental practitioner has time to trim the dental material to provide a custom fit onto the prepared tooth. During this time period, which is referred to herein as the extended flexible phase working time, the dental material preferably continues to harden to a hardness of 80 on a Shore A Durometer. After the dental material has been suitably modified to provide a custom fit in the mouth during this extended flexible phase, the dental material is allowed to harden further, preferably to a fully hardened state. Herein, the times of the initial set phase and the extended flexible working phase are measured at room temperature (approximately 20–25° C.). When the hardening occurs in the mouth, these times may be slightly shorter as a result of the higher temperature of the mouth (e.g., 30–38° C.).

Dental materials of the type described in detail herein are normally supplied to the dental practitioner in at least two separate parts. At least one of these parts contains at least one reducing agent, which is one component of a first initiator system and at least one other part contains at least one oxidizing agent, which is a second component of a first initiator system. In using the dental material, the dentist mixes the portions to produce a hardenable composition. The dentist places the freshly prepared hardenable composition into a tooth template (impression). The inventors have discovered that by carefully selecting the individual components of the dental material one or more of the following problems is solved: the material hardens too quickly to an unworkable state; the material hardens too quickly and locks into tooth undercuts; the material does not harden to a workable state in a sufficient period of time; and the material produces too much heat during curing for patient comfort.

Resin System

The resin system includes one or more hardenable organic resins capable of forming a hardened material having sufficient strength and hydrolytic stability to render them suitable for use in the oral environment. A suitable organic resin is hardenable (e.g., polymerizable) by a free radical mechanism and includes monomers, oligomers, and/or polymers. Preferably, at least some of the monomers, oligomers, and/or polymers include ethylenic unsaturation and are capable of undergoing addition polymerization. A suitable resin preferably includes at least one ethylenically unsaturated monomer (i.e., includes at least one carbon-carbon double bond).

Examples of suitable resin components include: mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, tris (hydroxyethylisocyanurate) trimethacrylate, the bis-acrylates and bis-methacrylates of polyethylene glycols of molecular weight 200–500, copolymerizable mixtures of acrylated monomers such as those of U.S. Pat. No. 4,652,274, and acrylated oligomers such as those of U.S. Pat. No. 4,642,126; unsaturated amides such as methylene bis-acrylamide, methylene bis-methacrylamide, 1,6-hexamethylene bis-acrylamide, diethylene triamine tris-acrylamide, and beta-methacrylamidoethyl methacrylate; and vinyl compounds such as styrene, diallyl phthalate, divinyl succinate, divinyl adipate, and divinylphthalate. Mixtures of two or more monomers, oligomers, and/or polymers in the resin system can be used if desired.

First Initiator System

The first initiator system is a redox initiator that includes an oxidizing agent (such as a peroxide) and a reducing agent (such as an aromatic amine). Combining the redox couple results in the generation of an initiating species (such as free radicals or cations) capable of causing curing (e.g., polymerization and/or crosslinking) of a hardenable resin. Preferably, the redox couples of this invention are activated at temperatures below about 40° C. Generally, the redox couple is partitioned into separate reactive compositions prior to use and then subsequently mixed at the time of use to generate the desired initiating species. Selection of the redox couple is governed by several criteria. For example, a desirable oxidizing agent is one that is sufficiently oxidizing in nature to oxidize the reducing agent, but not excessively oxidizing that it may prematurely react with resins or other components with which it may be combined during storage. Similarly, a desirable reducing agent is one that is sufficiently reducing in nature to readily react with the preferred oxidizing agent, but not excessively reducing in nature such that it may reduce the resin or other components with which it may be combined during storage. Oxidation or reduction of the resin with an inappropriate reducing agent or oxidizing agent, respectively, could result in an unstable system that would prematurely polymerize and subsequently provide a limited shelf life. Thus, suitable redox couples individually provide good shelf-life, and then, when combined together, generate the desired initiating species for hardening of the resin system.

Suitable oxidizing agents include peroxide compounds (i.e., peroxy compounds), including hydrogen peroxide as well as inorganic and organic peroxide compounds (e.g., "per" compounds or salts with peroxoanions). Examples of suitable oxidizing agents include, but are not limited to: peroxides such as benzoyl peroxide, phthaloyl peroxide, substituted benzoyl peroxides, acetyl peroxide, caproyl peroxide, lauroyl peroxide, cinnamoyl peroxide, acetyl benzoyl peroxide, methyl ethyl ketone peroxide, sodium peroxide, hydrogen peroxide, di-tert butyl peroxide, tetraline peroxide, urea peroxide, and cumene peroxide; hydroperoxides such as p-methane hydroperoxide, di-isopropylbenzene hydroperoxide, tert-butyl hydroperoxide, methyl ethyl ketone hydroperoxide, and 1-hydroxy cyclohexyl hydroperoxide-1, ammonium persulfate, sodium perborate, sodium perchlorate, potassium persulfate, etc.; ozone, ozonides, etc. These oxidizing agents may be used alone or in admixture with one another. Benzoyl peroxide is the preferred oxidizing agent. One or more oxidizing agents may be present in the first initiator system in an amount sufficient to provide initiation of the hardening process. Preferably, this includes about 0.01 weight percent (wt-%) to about 4.0 wt-%, and more preferably about 0.05 wt-% to about 1.0 wt-%, based on the total weight of all components of the dental material.

The first initiator system also includes a reducing agent with one or more functional groups for activation of the oxidizing agent and initiation of hardening. The functional groups provide both a fast and a slow rate of activation for the initiation of hardening for the initial set phase and extended flexible phase, respectively. Preferably, the functional groups are selected from amines, mercaptans, or mixtures thereof. If more than one functional group is present, they may be part of the same compound or provided by different compounds.

A preferred reducing agent is a tertiary aromatic amine. An example of the type of useful tertiary amines to the invention is

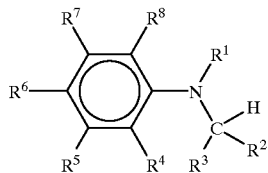

wherein each R group can be H or an organic group that does not adversely effect the initiation of hardening of the dental material. Preferably, the organic groups would not sterically or electronically hinder the function of the reducing agent. Examples of such compounds are disclosed in WO 97/35916, published Oct. 2, 1997.

As used herein, the term "organic group" means a hydrocarbon group (with optional elements other than carbon and hydrogen, such as oxygen, nitrogen, sulfur, and silicon) that is classified as an aliphatic group, cyclic group, or combination of aliphatic and cyclic groups (e.g., alkaryl and aralkyl groups). It also includes functional groups such as carboxylic acid groups, esters, amides, and the like. The term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated linear or branched hydrocarbon group with one or more carbon-carbon double bonds, such as a vinyl group. The term "alkynyl group" means an unsaturated linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

Substitution is anticipated on the organic groups of the compounds described herein. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, Si, or S atoms, for example, in the chain (as in an alkoxy group) as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like.

Referring to the tertiary amine described above, preferably $R^1$ is an aliphatic group and $R^2$ and $R^3$ are independently (i.e., they may be the same or different) H, aromatic and/or aliphatic groups (preferably including up to 20 carbon atoms). Preferably, only one of $R^2$ and $R^3$ is an aromatic group. More preferably, $R^1$ is an alkyl group (preferably including up to 10 carbon atoms) optionally substituted with hydroxy groups, and $R^2$ and $R^3$ are H or alkyl groups (preferably including up to 10 carbon atoms) optionally substituted with hydroxyl groups. For certain preferred embodiments, $R^1$, $R^2$, and $R^3$ can also include a polymerizable functional group that will react with the functional groups of the resin. Preferably, at least one of $R^1$, $R^2$, and $R^3$ includes a functional group such as an acrylate, methacrylate, acrylamide, vinyl, or other functional group present in the resins described above.

Preferably, $R^4$, $R^5$, $R^6$, $R^7$, and $R^8$ are independently H or aliphatic groups (preferably including up to 20 carbon atoms). More preferably, $R^4$, $R^5$, $R^6$, $R^7$, and $R^8$ are independently H or alkyl groups (preferably including up to 10 carbon atoms) optionally substituted with hydroxy groups. For certain preferred embodiments, $R^4$, $R^5$, $R^6$, $R^7$, and $R^8$ can also include a polymerizable functional group that will react with the functional groups of the resin. Preferably, at least one of $R^4$, $R^5$, $R^6$, $R^7$, and $R^8$ includes a functional group such as an acrylate, methacrylate, acrylamide, vinyl, or other functional group present in the resins described above.

Particularly preferred aromatic tertiary amines are N,N-bis(2-hydroxyethyl)-p-toluidine (DHEPT), 2-(4-dimethylaminophenyl)ethyl alcohol (DMAPE), 4-tert butyl dimethyl aniline. Other compounds that are suitable include compounds derived from DMAPE with di- or multifunctional acid compounds such as adipic acid, sebacic acid, 1,3,5-benzene tricarboxylic acid, 1,2,4,5-benzene tetracarboxylic acid, and the like, or DMAPE with di- or multifunctional isocyanates such as hexamethylene diisocyanate, isophorone diisocyanate, and desmodur N-330 (a trifunctional isocyanate).

The tertiary amines may be polymerizable. Particularly preferred polymerizable aromatic tertiary amines include, but are not limited to, an adduct of IEM (2-isocyanatoethylmethacrylate) with N,N-bis(2-hydroxyethyl)-p-toluidine (DHEPT-di-IEM or bis-N,N-[2-(2-methacryloloxyethylaminocarbonyloxy)ethyl]-p-toluidine), an adduct of DMAPE with VDM (2-vinyl-4,4-dimethylazlactone) (DMAPE-VDM or 4-[2(2-acrylamido-2-methylpropionyloxy)ethyl)-N,N-dimethlyaniline), an adduct of a methacrylate di-ester with DHEPT (DHEPT-di-ester or bis-N,N-(2-methacryloloxyethyl)-p-toluidine), and an adduct of DHEPT with VDM (DHEPT-di-VDM or bis-N,N-[2-(2-acrylamido-2-methylpropionyloxy)ethyl]-p-toluidine).

Another preferred reducing agent is a mercaptan, which can include aromatic and/or aliphatic groups, and optionally polymerizable groups. Preferred mercaptans have a molecular weight greater than about 200 as these mercaptans have less odor. Particularly preferred mercaptans are isooctylthioglycoate (IOTG) and pentaerythritol tetrakis (3-mercaptopropionate) (PETMP).

The tertiary amines and mercaptans may be used alone or in admixture with one another. For example, the first initiator system can include one tertiary aromatic amine and one mercaptan, two tertiary aromatic amines, two mercaptans, one polymerizable tertiary aromatic amine, and the like. Other reducing agents, such as sulfinic acids, formic acid, ascorbic acid, hydrazines, and salts thereof, can also be used herein to initiate free radical polymerization. Preferably, however, the first initiator system includes a tertiary aromatic amine, a mercaptan, or a mixture thereof. Such reducing agents can function as both a component of the first initiator system and a component of the second initiator system.

If two or more reducing agents are used, they are preferably chosen such that at least one has a faster rate of activation than the other(s). That is, one causes a faster rate of initiation of the hardening of the resin than the other(s). Significantly, this provides for the two hardening stages referred to herein as the initial set phase and the extended flexible phase.

Electrochemical oxidation potentials of reducing agents and reduction potentials of oxidizing agents are useful tools for predicting the effectiveness of a suitable redox couple. For example, the reduction potential of the oxidant (i.e., oxidizing agent) benzoyl peroxide is approximately –0.16 volts vs. a saturated calomel electrode (SCE). Similarly, the oxidation potential (vs. SCE) for a series of amines has been previously established as follows: dihydroxyethyl-p-toluidine ((DHEPT), 0.76 volt), 4-t-butyl dimethylaniline ((t-BDMA), 0.77 volt), 4-dimethylaminophenethanol ((DMAPE), 0.78 volt), triethylamine ((TEA, 0.88 volt), 3-dimethylaminobenzoic acid ((3-DMAB) 0.93 volt), 4-dimethylaminobenzoic acid ((4-DMAB, 1.07 volts), ethyl p-dimethylaminobenzoate ((EDMAB), 1.07 volts), 2-ethylhexyl p-dimethylaminobenzoate ((EHDMAB), 1.09 volts) and 4-dimethylaminobenzoate ((DMABA), 1.15 volts). The ease of oxidation (and subsequent reactivity) increases as the magnitude of the oxidation decreases. Suitable amine reducing agents in combination with benzoyl peroxide generally include aromatic amines with reduction potentials less than about 1.00 volt vs. SCE. Less effective oxidants than benzoyl peroxide such as lauroyl peroxide (reduction potential=–0.60 volt) are poorer oxidizing agents and subsequently react more slowly with aromatic amine reducing agents. Suitable aromatic amines for lauroyl peroxide will generally include those less than about 0.80 volt vs SCE.

In systems in which two or more reducing agents are present, the relative amounts of each are such that the faster reducing agent(s) is preferably substantially consumed prior to the slower reducing agent(s). Typically, the relative amounts depend on their relative rates of initiation, as well as the types and amounts of other components. Given the disclosure presented herein, one skilled in the art can determine what these amounts should be without undue experimentation. Preferably, the faster reducing agent is present in an amount of about 0.01 wt-% to about 4.0 wt-%, and the slower reducing agent is present in an amount of about 0.01 wt-% to about 4.0 wt-%, based on the total weight of all the components of the dental material. More preferably, the faster reducing agent is present in an amount of about 0.02 wt-% to about 2.0 wt-%, and the slower reducing agent is present in an amount of about 0.02 wt-% to about 2.0 wt-%, based on the total weight of all the components of the dental material. The total amount of reducing agent, based on the weight percent of all the components of the dental material, is preferably within a range of about 0.02 wt-% to about 5.0 wt-%, and more preferably within a range of about 0.1 wt-% to about 3.0 wt-%.

If the reducing agent is a polymerizable tertiary amine, no other reducing agents are required, although others can be used if desired. Surprisingly, a polymerizable tertiary amine reducing agent provides differential initiation rates of the hardening of the resin. The amount of the polymerizable tertiary amine, based on the weight percent of all the components of the dental material, is preferably within a range of about 1.0 wt-% to about 25.0 wt-%, and more preferably within a range of about 2.0 wt-% to about 15.0 wt-%.

Second Initiator System

The dental material of the present invention preferably includes a second initiator system. The second initiator system includes one or more initiators commonly used in free radical polymerization. The function of the second initiator system is to further harden the dental material upon completion of the extended flexible phase work time. The initiators are preferably free radical initiators, which may be activated in a variety of ways, e.g., heat and/or radiation. Thus, the second initiator system can be a redox initiator system, a thermal initiator system (e.g., azo compounds and peroxides), or a photoinitiator system, for example. This final hardening stage of the dental material preferably occurs outside of the oral environment.

Preferably, the second initiator system includes one or more photoinitiators. More preferably, the second initiator system includes at least one photoinitiator active in the spectral region of about 300 nanometers (nm) to about 1200 mn and capable of promoting free radical polymerization and/or crosslinking of ethylenically unsaturated moieties upon exposure to light of suitable wavelength and intensity. A wide variety of such photoinitiators can be used. Preferably, they are sufficiently shelf stable and free of undesirable coloration to permit storage and use under typical dental conditions. Visible light photoinitiators are preferred.

One type of suitable second initiator system is described in U.S. Pat. No. 5,545,676, which includes a three component or ternary photoinitiator system. This system includes an iodonium salt, e.g., a diaryliodonium salt, which can be a simple salt (e.g., containing an anion such as $Cl^-$, $Br^-$, $I^-$, or $C_4H_5SO_3^-$) or a metal complex salt (e.g., containing $SbF_5OH^-$ or $AsF_6^-$). Mixtures of iodonium salts can be used if desired. The second component in this ternary photoinitiator system is a sensitizer, which is capable of light absorption somewhere within the range of wavelengths of about 400 nm to about 1200 nm. The third component in this ternary photoinitiator system is an electron donor and includes amines (including aminoaldehydes and aminosilanes or other amines as described for the first initiator system), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid.

Examples of sensitizers suitable for use in the ternary photoinitiator system include ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes, and pyridinium dyes.

Ketones (e.g., monoketones or alpha-diketones), ketocoumarins, aminoarylketones, and p-substituted aminostyryl ketone compounds are preferred sensitizers. Examples of particularly preferred visible light sensitizers include camphorquinone, glyoxal, biacetyl, 3,3,6,6-tetramethylcyclohexanedione, 3,3,7,7-tetramethyl-1,2-cycloheptanedione, 3,3,8,8-tetramethyl-1,2-cyclooctanedione, 3,3,18,18-tetramethyl-1,2-cyclooctadecanedione, dipivaloyl, benzil, furil, hydroxybenzil, 2,3-butanedione, 2,3-pentanedione, 2,3-hexanedione, 3,4-hexanedione, 2,3-heptanedione, 3,4-heptanedione, 2,3-octanedione, 4,5-octanedione, and 1,2-cyclohexanedione. Of these, camphorquinone is the most preferred sensitizer.

Yet another type of photoinitiator includes acylphosphine oxides, such as those described in European Pat. Application No. 173567. Suitable acylphosphine oxides are preferably of the general formula $(R^9)_2—P(=O)—C(=O)—R^{10}$, wherein each $R^9$ is individually a hydrocarbon group, preferably an alkyl group, alicyclic group, aryl group, and aralkyl group, any of which can be substituted with a halo-, alkyl- or alkoxy-group, or the two $R^9$ groups can be joined to form a ring along with the phosphorous atom, and wherein $R^{10}$ is a hydrocarbon group, preferably, a S-, O-, or N-containing five- or six-membered heterocyclic group, or a —Z—C(=O)—P(=O)—$(R^9)_2$ group, wherein Z represents a divalent hydrocarbon group such as alkylene or phenylene having from 2 to 6 carbon atoms. Examples of suitable acylphosphine oxides include bis(2,4,6-trimethylbenzoyl) phenyl phosphine oxide, for example. Optionally, tertiary amine reducing agents may be used in combination with an acylphosphine oxide. Illustrative tertiary amines useful in the invention include those described above as well as ethyl 4-(N,N-dimethylamino)benzoate and N,N-dimethylaminoethyl methacrylate.

Mono- and di-ketones can also be used as photoinitiators. Examples of such systems are described in U.S. Pat. No. 4,071,424, for example.

Still another class of photoinitiators includes ionic dye-counterion complex initiators that include a borate anion and a complementary cationic dye. Borate anions useful in these photointiators generally can be of the formula $(R^{11})_4^-$ wherein each $R^{11}$ is independently an alkyl, aryl, alkaryl, allyl, aralkyl, alkenyl, alkynyl, alicyclic, and saturated or unsaturated heterocyclic groups. Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. Quaternary ammonium groups useful as counterions can be trimethylcetylammonium, cetylpyridinium, and tetramethylammonium. Other organophilic cations can include pyridinium, phosphonium, and sulfonium. Cationic transition metal coordination complexes that may be useful as counterions can be complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri(2-pyridyl-s-triazine) and related ligands. Borate salt photoinitiators are described, for example, in U.S. Pat. Nos. 4,772,530, 4,954,414, 4,874,450, 5,055,372, and 5,057,393.

Preferred visible light-induced initiators include camphorquinone combined with a suitable hydrogen donor (e.g., an amine such as those described above for the first initiator system), and optionally a diaryliodonium simple or metal complex salts, chromophore-substituted halomethyl-s-triazines, and halomethyl oxadiazoles. Particularly preferred visible light-induced photoinitiators include combinations of an alpha-diketone, e.g., camphorquinone with additional hydrogen donors, and optionally a diaryliodonium salt, e.g., diphenyliodonium chloride, bromide, iodide or hexafluorophosphate.

If present, the initiator is included in the dental material in an amount sufficient to provide the desired rate of hardening. Typically, this amount is dependent in part on the light source, the thickness of the layer to be exposed to radiant energy, and the extinction coefficient of the initiator. Preferably, an initiator is present at an amount of about 0.01 wt-% to about 5 wt-%, and more preferably from about 0.03 wt-% to about 1.0 wt-%, based on the total weight of the dental material.

Filler System

A filler system includes one or more fillers and may be selected from one or more materials suitable for incorporation in medical applications, such as the fillers currently used in dental materials. The filler is preferably finely divided with an average particle size (i.e., the longest dimension of the particle, such as the diameter) of no greater than about 10 micrometers and a maximum particle size of no greater than about 50 micrometers. The filler can have a unimodal or polymodal (e.g., bimodal) particle size distribution. The filler can be an inorganic material or it can also be a crosslinked organic material that is insoluble in the resin system. The filler can be radiopaque, radiolucent, or non-radiopaque.

Examples of suitable inorganic fillers include naturally occurring or synthetic materials such as quartz, nitrides (e.g., silicon nitride), glasses derived from, for example, Ce, Sb, Sn, Zr, Sr, Ba, or Al, colloidal silica, feldspar, borosilicate glass, kaolin, talc, titania, and zinc glass, zirconia-silica fillers; low Mohs hardness fillers such as those described in U.S. Pat. No. 4,695,251; and submicron silica particles (e.g., pyrogenic silicas such as those available under the trade designation "AEROSIL" such as "OX 50," "OX 130," "OX 150," and "OX 200" from Degussa, Ridgefield Park, N.J., and "Cab-O-Sil M5" silica from Cabot Corp., Boston, Mass.). Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169. Mixtures of these fillers are also contemplated, as well as combination fillers made from organic and inorganic materials. Fluoroaluminosilicate glass fillers, either untreated or silanol treated, are particularly preferred. These glasses have the added benefit of releasing fluoride at the site of dental work when placed in the oral environment.

Fillers are preferably chosen to enhance certain properties, such as compressive strength, diametral tensile strength, wear resistance, appearance, translucency, radioopacity, and storage stability of the dental materials, as well as to limit exothermic effects during the initial set phase.

Optionally, the surface of the filler particles may be treated with a surface treatment, such as a silane coupling agent, in order to enhance the bond between the filler and the resin system. The coupling agent may be functionalized with reactive curing groups, such as acrylates, methacrylates, and the like.

Preferably, the total amount of filler is about 2.0 wt-% to about 80.0 wt-%, based on the total weight of the components of the dental material. More preferably, the total amount of filler is about 30.0 wt-% to about 70.0 wt-%, based on the total weight of the components of the dental material.

Optional Additives

Dental materials of the present invention may additionally include optional adjuvants such as colorants (e.g., pigments conventionally used for shade adjustment), flavorants, medicaments, stabilizers (such as BHT and Tinuvin P), viscosity modifiers, and the like. Such adjuvants may optionally include reactive functionality so that they will be copolymerized with the resin.

Method of Using the Dental Material

A preferred method of using the dental material of the invention includes the following steps: 1) make an impression (e.g., an alginate impression) before preparing the tooth (or teeth); 2) prepare the tooth (or teeth); 3) mix the components of the dental material to form a hardenable composition; 4) fill the impression with the hardenable composition (preferably this occurs simultaneously while mixing the components); 5) place the impression over the tooth (or teeth) and allow the hardenable composition to partially harden to a sufficient hardness to be removable from the mouth without being permanently deformed, but not so rigid that the solidified impression locks into undercuts and becomes too hard and brittle to be trimmed.; 6) remove the impression and hardened composition from the mouth; 7) trim the excess hardened material; 8) reseat the restorative in the mouth to ensure correct fit; 9) allow the restorative to further harden, and if necessary apply heat or light; 10) conduct final trimming, polishing, and cleaning of the restorative; and 11) cement the restorative into place within the mouth.

Typically, the dental material is provided to the dental practitioner in at least two parts, wherein the reducing agent(s) and the oxidizing agent(s), which form the first initiator system are separate. Preferably, there are two parts, each one may include a portion of the resin system and a portion of the filler system. The reducing agent(s) is included in one and the oxidizing agent(s) in the other. The components of the second initiator system can be in either part as long as there is no reaction with the oxidizing and the reducing agents of the first initiator system. Thus, kits are provided by the present invention that include a container for each part. Preferably, two containers are provided in a dual-compartment cartridge, optionally including a static mixing tip, that is used in combination with a hand-held dispenser. Such cartridges and dispensers are commercially available such as that available from Mixpac Systems, Switzerland.

The following examples are given to illustrate, but not limit, the scope of this invention. Unless otherwise indicated, all parts and percentages are by weight and all molecular weights are weight average molecular weight.

Test Methods and Preparation of Materials

Diametral Tensile Strength (DTS) and Compressive Strength (CS) Testing

ADA ("American Dental Association") specification No. 9 and ADA specification No. 27, respectively, of ISO-test procedure 4049 (1988) were followed for all diametral tensile strength (DTS) and compression strength (CS) testing. Specifically, for CS and DTS testing, the composition was packed into a 4 millimeter (mm) (inside diameter) glass tube, capped with silicone rubber plugs and axially compressed at about 0.28 megapascals (Mpa) for 15 minutes, then light cured for 80 seconds by exposure to two oppositely-disposed VISILUX units (VISILUX 2, 3M St. Paul, Minn.). Each sample was then irradiated for 90 seconds using a Dentacolor XS unit (Kulzer, Inc., Germany). Cured samples were cut on a diamond saw to form cylindrical plugs 8 mm long for measurement of CS and 2 mm long for measurement of DTS. The plugs were stored in distilled water at 37° C. for 24 hours. CS and DTS values for each composition were measured using an INSTRON tester (Instron 4505, Instron Corp., Canton, Mass.).

The Compressive Strength (CS) of these samples was tested on an INSTRON tester with a 10-kN load cell. A total of 5 cylinders of cured composite with about 8 mm length and 4 mm diameter were prepared.

The Diametral Tensile Strength (DTS) of these samples was tested on an INSTRON tester with 10-kN (kilonewton) load cell. A total of 5 cylinders of cured composite with about 2.2 mm length and 4 mm diameter were prepared.

Measurement of Barcol Hardness

Samples of each composite were cured in 2.0 mm thick steel molds sandwiched between polyester (PET) film and glass slides for 60 seconds each with a VISILUX 2 (3M Co., St. Paul, Minn.). After irradiation, the PET films were removed and the hardness of the sample at the bottom of the mold was measured using a Barber-Coleman Impressor (a hand-held portable hardness tester; Model GYZJ 934-1; Barber-Coleman Co. Industrial Instruments Division, Lovas Park, Ind.) equipped with an indenter. Top and bottom Barcol hardnesses were measured at 5 minutes and at 24 hours after light exposure.

For each composition tested, three readings were taken on the top face and three readings were taken on the bottom face of each sample. The readings were averaged for each composition.

Measurement of Shore A Hardness

A 10 centimeter (cm)×10 cm×1 cm slab of glass was covered with a similar sized stretchable plastic sheet (PARAFILM, American National Can, Neenah, Wis.). Then a 2.5-mm thick stainless steel ring, having an outer diameter of 57 mm and an inner diameter of 31 mm, was placed on top of the 10 cm×10 cm slab of glass. A black dual 1:1 compartment cartridge (Part No. CS 050-01-13, Mixpac Systems, Switzerland), containing the restorative paste to be tested, was fitted to a hand held dispenser (Mixpac Systems, Switzerland). The base paste containing a reducing agent was loaded into one of the compartments and the paste containing an oxidizing agent was loaded into the other compartment prior to testing. The outlet ports of both chambers were drained and then a static mix tip (MBX-4.2-16-S Mixpac Systems, Switzerland) was fitted to the cartridge. This static mixing tip allowed the base paste and the oxidizing agent paste, contained in the two separate chambers of the cartridge, to be mixed homogeneously when the pastes were extruded by means of the hand dispenser.

Approximately 2 mL of paste was extruded inside the inner circle of the previously mentioned stainless steel ring. At this point the stopwatch was started. A second piece of stretchable plastic sheet was placed on top of the fresh paste which had been deposited within the aforementioned stainless steel ring, and the excess paste was squeezed out by means of placing a second 10 cm×10 cm×1 cm of glass on top of the stretchable plastic sheet and stainless steel ring. This upper glass slab was removed after 45 seconds. Then a Shore Durometer Hardness Tester, type A2 (The Shore Instrument and Manufacturing Co. in NY, N.Y.) was used to measure hardness as a function of time.

Determination of Initial Set Phase Time ($T_{20}$) and Extended Flexible Phase Work Time (Delta T)

When time vs. hardness is plotted on an X-Y diagram then an S-shaped curve is obtained. From this chart "$T_{20}$" and "$T_{80}$" can be defined as the time required to achieve a Shore A hardness of 20 and 80, respectively. An additional value, "Delta T" is obtained by subtracting $T_{20}$ from $T_{80}$. $T_{20}$ and Delta T represent the initial set phase time and the extended flexible phase work time, respectively.

| Abbreviations/Definitions | |
|---|---|
| Aerosil R-972 | pyrogenic silica (Degussa Corporation, Akron, Ohio) |
| BHT | 2,6-Di-tert-butyl-4-methylphenol |
| Bis-GMA | 2,2-bis[4(2-hydroxy-3-methacryloyloxy-propyloxy)-phenyl]propane |
| Bis-EMA-6 | 6 mole ethoxylated bisphenol A dimethacrylate |
| BPO | benzoylperoxide |
| CPQ | camphorquinone |
| CS | Compressive Strength |
| DMAPE | 2-(4-Dimethylaminophenyl)ethyl alcohol |
| DMAPE-VDM | adduct of DMAPE with 2-vinyl-4,4-dimethylazlactone) |
| DHEPT-di-ester | methacrylate di-ester adduct of DHEPT |
| DTS | Diametral Tensile Strength |
| IEM | 2-isocyanatoethylmethacrylate |
| IOTG | isooctylthioglycoate |
| PETMP | pentaerythritol tetrakis (3-mercaptopropionate) |
| TEGDMA | triethyleneglycol dimethacrylate |
| Tinuvin P | 2(2'-hydroxy 5'-methylphenyl) benzotriazole (UV stabilizer) |
| UDMA | diurethane dimethacrylate ("ROHAMERE 6661-0" from Monomer Polymer and Dajae Labs, Inc., Feasterville, PA) |
| ISOTEMP | temporary dental material (3M, St. Paul, MN) |
| TEMPHASE | temporary dental material (SDS Kerr, Orange, CA) |
| LUXATEMP | temporary dental material (DMG, Foremost Dental, Englewood, NJ) |
| Cab-O-Sil M-5 | pyrogenic silica (Cabot Corp. Tuscola, IL) |
| Tween-40 | polyoxyethylene 20 sorbitan monopalmitate (Sigma-Aldrich Corp., Milwaukee, WI) |

Synthesis of DBEPT-di-IEM

N,N-Bis(2-hydroxyethyl)-p-toluidine (DHEPT, 100 grams (g), 0.512 mole (mol)), BHT (0.45 g, 2.042 mmol), and dibutyltin dilaurate reducing agent (0.32 g, 0.507 millimole (mmol)) were dissolved in 250 milliliter (mL) tetrahydrofuran in a 3-neck round bottom flask equipped with a mechanical stirrer under a nitrogen atmosphere. 2-Isocyanatoethylmethacrylate (IEM, Dow Chemical, Midland, Mich., 159.7 g, 1.029 mol) was added dropwise to this solution at ambient temperature. The mixture was cooled to 16° C. in an ice bath, while being stirred efficiently. Stirring was continued for an hour during which time the temperature rose to 33° C. The temperature dropped to 29° C. within a hour, and then further to 26° C. after another hour. Stirring was continued overnight, approximately 16–18 hours at room temperature. At this point the reaction was stopped and no urethane band could be detected by IR spectroscopy. Then 50 mL of methanol was added to the mixture and mixed for 2 hours. The solvents were finally removed under vacuum at 35° C. to obtain 261.1 g DHEPT-di-IEM (adduct of IEM with N,N-Bis(2-hydroxyethyl)-p-toluidine—N,N'-bis(2-[2-methacryloyloxyethylcarbamyl] ethyl)-p-toluidine.

Preparation of Silane $ZrO_2SiO_2$ Filler

The $ZrO_2SiO_2$ Filler was prepared as follows: 25.5 parts silica sol (LUDOX LS, E. I. duPont de Nemours & Co., Wilmington, Del.) were first diluted with 8.8 parts deionized water and then acidified by addition of 0.95 part concentrated nitric acid using vigorous agitation to make the solution homogenous. In a separate vessel, 12.9 parts zirconyl acetate (Magnesium Elektron, Inc., Flemington, N.J.) were diluted with 6.2 parts deionized water. The acidified silica sol was pumped into the rapidly stirred zirconyl acetate solution over a 45 minute period. The stirred mixture was recirculated through a 3-micrometer filter followed by a 1-micrometer filter during the 45 minute addition of the silica sol to the zirconyl acetate. The filtered mixture was then spray dried (Niro 3-foot Mobile MINOR Spray Drier, Columbia, Md.)) using 325° C. inlet temperature, 120° C. outlet temperature, and an atomizer speed of 18,750 rpm (revolutions per minute). The spray dried filler was then placed in ceramic saggers and calcined at a soak temperature of 550° C. using an electric furnace (L & L Special Furnace Corp., Aston, Pa.). The calcined filler was comminuted in a tumbling ball mill with 6.35 mm (0.25 inch) alumina media until an average particle size of 0.5–1.2 micrometers (Sedigraph Model 5100, Micrometrics, Norcross, Ga.) was obtained; the mill charge included 75 parts calcined material, 1.5 parts methanol, 1.9 parts benzoic acid, and 1.1 parts deionized water. The filler was then loaded into ceramic saggers and fired in an electric furnace (L&L Special Furnace Corp.) in air at 900–950° C. for approximately 8 hours. The fired filler was then ball-milled for 5–10 hours; the mill charge included 32 parts fired filler, 1.25 parts ethanol, and 0.3 part deionized water. Next the filler was passed through a 74-micrometer nylon screen in a vibratory screener (Vortisiv V/S 10010 Salem, Ohio); the filler was then blended in a V-blender (Patterson-Kelly Corp. East Stroudsburg, Pa.) for about 15 minutes.

Preparation of Silane-treated Quartz Filler

Quartz filler (Coleman Quartz, Jessieville, Ark.) was heated to about 660° C., quenched in water, drained, then dried in a forced air oven for 16 hours at about 93° C. The quenched quartz and methane (99 parts quartz and 1 part methanol) was combined with quartz media in a mill and tumbled for about 20 hours. The resulting particles were blended with 0.1 wt.% carbon black in a PK-blender (Patterson-Kelly, Stroudsberg, Pa.) for 1 hour, then fired in an electric furnace at about 950° C. for 4 hours. The filler was then blended for another 30 minutes in a PK blender to obtain a fired quartz filler.

To 506 g of the above fired quartz filler was added 21 g Cab-O-Sil M5 fumed silica (Cabot Corporation, Tuscola, Ill.) and blended for 60 minutes using a PK Blender.

A 527 g portion of deionized water was weighed into a rigid vessel. The pH was adjusted to 3.0 to 3.5 with acetic acid (Aldrich Chem. Co., Milwaukee, Wis.) and mixing continued for five minutes. A 26.35 gram portion of 3-methacryloxypropyltrimethoxysilane available under the trade designation A-174 (Witco, South Charleston, W.V.), was heated to about 26–29° C., slowly added to the water, and mixed for 45 minutes until a clear solution was obtained.

The blend of fired quartz filler with Cab-O-Sil M5 fumed silica was added to the water and silane solution. The resultant slurry was mixed for 2 hours followed by drying for 24 hours at 38° C. The dried filler was crushed into a coarse powder and dried for an additional 2 hours at 110° C. This filler was screened through a 100 micron sieve and dried for an additional 16 hours at 38° C. After drying, the filler was screened through a 220 micron sieve and then stored until use.

EXAMPLES

Comparative Examples 1C–3C

Comparative Examples 1C, 2C, and 3C represent three methacrylate resin based, temporary crown and bridge materials available under the trade designations ISOTEMP, TEMPHASE, and LUXATEMP. Measurement of Shore A hardness as a function of time for these materials is shown in FIG. 1. Initial set phase time and extended flexible phase work time were calculated for all materials, as summarized in Table 1.

TABLE 1

Cure rates of three commercially available temporary materials

| Example | Material | Sample | $T_{20}$ [sec] | $T_{80}$ [sec] | Delta T [sec] |
|---|---|---|---|---|---|
| 1C | ISOTEMP | A | 210 | 343 | 133 |
|  |  | B | 244 | 410 | 166 |
| 2C | TEMPHASE | A | 145 | 201 | 56 |
|  |  | B | 136 | 185 | 49 |
| 3C | LUXATEMP | A | 87 | 152 | 65 |
|  |  | B | 96 | 165 | 69 |

Figure 2:
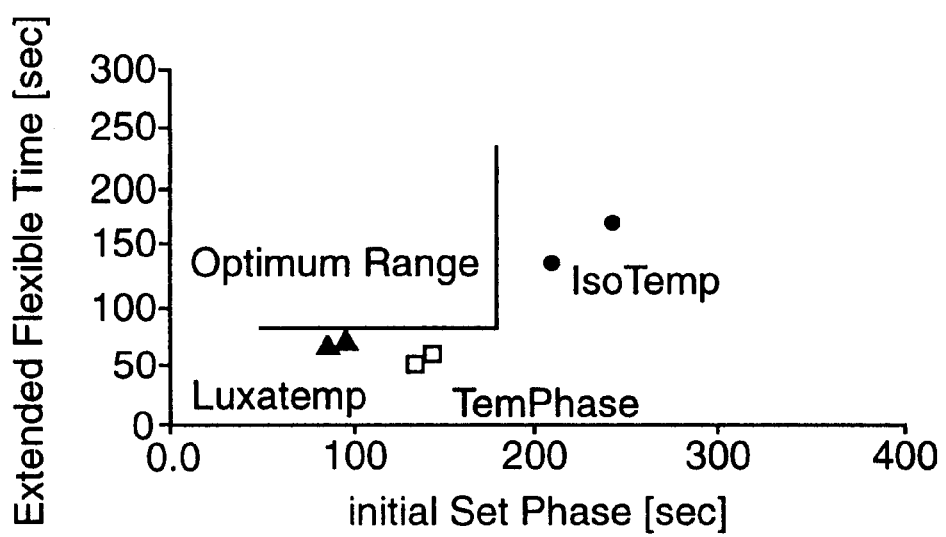
FIG. 2 is a chart of the initial set phase and extended flexible phase times of three comparative dental materials.

Initial set phase set time and extended flexible phase work time can be compared in a more convenient way, as shown in FIG. 2. Both TEMPHASE and LUXATEMP have a short initial set phase time, but lack a sufficiently long extended flexible phase stage. ISOTEMP, in contrast, has a long extended flexible phase stage, but a shorter initial set phase time would be preferred. An optimum combination of initial set phase vs. extended flexible phase work time is shown in FIG. 2.

Comparative Examples 4C-6C

Comparative Examples 4C, 5C, and 6C were all made with the same base (reducing agent) paste but three different oxidizing agent pastes.

The base paste was prepared by first dissolving 1.2 g Tinuvin P, 6.75 g DHEPT, and 0.008 g BHT in 150 g of a methacrylate monomer blend consisting of 38.04 g of a 90/10 by weight solution of Bis-GMA in TEGDMA, 17.39 g TEGDMA, 84.78 g UDMA, and 9.78 g Bis-EMA-6. A clear solution was obtained after stirring the mixture for four hours at 55° C. to 60° C. Subsequently, 176.1 g of silane treated $ZrO_2SiO_2$ filler was added and the composition was mechanically stirred for 30 minutes at 100 rpm until a homogeneous paste was obtained. The obtained base paste was filled into one compartment of a black, 1:1 dual cartridge (part # CS 050-01-13) obtained from Mixpac systems, Switzerland.

The three oxidizing agent pastes were prepared individually by dissolving 0.021 g BHT, 0.075 g CPQ, and an appropriate amount of BPO, as shown in Table 2, in a 30 g methacrylate monomer blend as described above for the base paste. A clear solution was obtained after mechanically stirring for 4 hours at room temperature. Subsequently, 35.2 g of silane-treated $ZrO_2SiO_2$ filler was added to the solution and mechanically stirred for 30 minutes at 100 rpm until a homogeneous paste was obtained. The obtained oxidizing agent paste was filled into the other compartment of the aforementioned black dual 1:1 compartment cartridge. Measurement of Shore A hardness for these materials to attain a reading of 20 and 80 as a function of time was collected for each of two samples (labeled A and B).

TABLE 2

Comparative examples demonstrating effects of increasing BPO level

| Example | BPO (g) | Sample | $T_{20}$ [sec] | $T_{80}$ [sec] | Delta T [sec] |
|---|---|---|---|---|---|
| 4C | 0.15 | A | 298 | 357 | 59 |
|  |  | B | 266 | 337 | 71 |
| 5C | 0.188 | A | 184 | 216 | 32 |
|  |  | B | 177 | 209 | 32 |
| 6C | 0.225 | A | 143 | 175 | 32 |
|  |  | B | 139 | 169 | 30 |

Amounts of BPO refer to grams in 30 grams of previously described methacrylate monomer blend in the oxidizing agent paste.

Comparative Examples 7C and 8C

Comparative Examples 7C and 8C were made with the same base (reducing agent) paste prepared previously for Comparative Examples 4C-6C. The base pastes were filled into one side of the black 1:1 dual compartment cartridges.

The two oxidizing agent pastes were prepared separately by dissolving 0.075 g CPQ, 0.188 g BPO, and an appropriate amount of BHT, as shown in Table 3, in a 30 g methacrylate monomer blend. The composition of the monomer blend was identical to that of the monomer blend described in Comparative Example 4C base paste. A clear solution was obtained after stirring for 4 hours at room temperature. Subsequently 35.2 g of a silane-treated $ZrO_2SiO_2$ filler was added to the solution and mechanically stirred for 30 minutes at 100 rpm until a homogeneous paste was obtained. The obtained oxidizing agent paste was filled into the other compartment of the aforementioned black 1:1 dual compartment cartridge. Measurement of Shore A hardness for these materials to attain a reading of 20 and 80 as a function of time was collected for each of two samples.

TABLE 3

Comparative examples demonstrating effects of increasing BHT level

| Example | BHT (g) | Sample | $T_{20}$ [sec] | $T_{80}$ [sec] | Delta T [sec] |
|---|---|---|---|---|---|
| 7C | 0.015 | A | 126 | 160 | 34 |
|  |  | B | 126 | 159 | 33 |
| 8C | 0.027 | A | 280 | 319 | 39 |
|  |  | B | 261 | 311 | 50 |

Amounts of BHT refer to grams of BHT in 30 grams of the methacrylate monomer blend of described in Comparative Example 4C in the oxidizing agent paste.

Comparative Examples 9C-11C

Comparative Examples 9C, 10C, and 11C were all made with the same oxidizing agent paste but three different base (reducing agent) pastes.

The oxidizing agent paste was prepared by dissolving 0.127 g BHT, 0.455 g CPQ, and 1.138 g of BPO in a 182 g of the methacrylate monomer blend. The composition of the monomer blend was identical to that of the monomer blend described in Comparative Example 4C base paste. A clear solution was obtained after stirring for 4 hours at room temperature. Subsequently, 213.6 g of silane treated $ZrO_2SiO_2$ filler was added to it and mechanically stirred for 30 minutes at 100 rpm until a homogeneous paste was obtained. The obtained oxidizing agent paste was filled into one compartment of a black 1:1 dual cartridge.

The three base pastes were prepared individually by first dissolving 0.24 g Tinuvin P, 0.0015 g BHT, and an appropriate amount of DHEPT, as shown in Table 4, in 30 g of a methacrylate monomer blend. The composition of the monomer blend was identical to that of the monomer blend described in Comparative Example 4C base paste. The solution was obtained by stirring for four hours at 55° C. to 60° C. Subsequently, 35.2 g of silane-treated $ZrO_2SiO_2$ filler was added to it and mechanically blended until a homogeneous paste was obtained. The obtained base paste was filled into the other compartment of the aforementioned black 1:1 dual compartment cartridge. Measurement of Shore A hardness for these materials to attain a reading of 20 and 80 as a function of time was collected for each of two samples.

TABLE 4

Comparative examples demonstrating effects of increasing DHEPT level

| Example | DHEPT (g) | Sample | $T_{20}$ [sec] | $T_{80}$ [sec] | Delta T [sec] |
|---|---|---|---|---|---|
| 9C | 0.9 | A | 279 | 358 | 79 |
|  |  | B | 257 | 339 | 82 |
| 10C | 1.35 | A | 224 | 270 | 46 |
|  |  | B | 200 | 234 | 34 |
| 11C | 1.65 | A | 186 | 214 | 28 |
|  |  | B | 163 | 194 | 31 |

Amounts of DHEPT refer to grams in 30 grams of the methacrylate monomer blend of described in Comparative Example 4C monomer blend in the base paste.

Examples 12–17

Base (reducing agent) paste for Example 12 was made by preparing a first solution of 0.006 g BHT, 0.96 g Tinuvin P, and 2.508 g of DHEPT in a 120 g of the methacrylate monomer blend, and a second solution of 0.005 g BHT, 0.84 g Tinuvin P, and 1.860 g of DMAPE in a 105 g methacrylate monomer blend. Both monomer blends had the same composition, which is identical to that of the monomer blend described in Comparative Example 4C base paste. The solution process required mechanical stirring for 2–4 hours at 55° C. to 60° C. Then, 9 g of the first solution and 26.9 g of the second solution were combined, and to the resulting solution was added 41.1 g of silane-treated $ZrO_2SiO_2$ filler. This was mechanically stirred for 30 minutes at 100 rpm until a homogeneous paste was obtained.

For Examples 13 and 14 the same base paste was used, which was prepared by dissolving 1.28 g Tinuvin P, 1.67 g DHEPT, and 1.42 g DMAPE in 160 g of a methacrylate monomer blend by stirring for 2–4 hours at 55° C. to 60° C. The composition of the monomer blend was identical to that of the monomer blend described in Comparative Example 4C base paste. Then 187.8 g of a silane-treated $ZrO_2SiO_2$ filler was added to it and mechanically stirred for 30 minutes at 100 rpm until a homogeneous paste was obtained.

Base (reducing agent) pastes for Examples 15–17 were identical in formulation and were prepared by first dissolving 2 g Tinuvin P, 2.613 g DHEPT, and 2.214 g DMAPE in 250 g of a methacrylate monomer blend by stirring for 2–4 hours at 55° C. to 60° C. The composition of the monomer blend was identical to that of the monomer blend described in Comparative Example 4C base paste. The three base pastes were then prepared individually by adding 47 g of silane-treated $ZrO_2SiO_2$ filler to each of 41.09 g of the above solution and mechanically stirred for 30 minutes at 100 rpm until a homogeneous paste was obtained. The so obtained base pastes were filled into one compartment of individual black 1:1 dual compartment cartridges.

Oxidizing agent pastes for Examples 12–17 were prepared individually by dissolving appropriate amounts of BHT, CPQ, and BPO in a methacrylate monomer blend at room temperature. The composition of the monomer blend was identical to that of the monomer blend described in Example 4C base paste. Then, silane-treated $ZrO_2SiO_2$ filler was added to it and mechanically blended until a homogeneous paste was obtained. Amounts of components used to make the individual oxidizing pastes are given in Table 5. The so obtained oxidizing agent pastes were filled into the other compartment of the aforementioned black 1:1 dual compartment cartridges. Measurement of Shore A hardness for these materials to attain a reading of 20 and 80 as a function of time was collected for each of two samples.

TABLE 5

Composition of oxidizing agent pastes for Examples 12–17

| Example | BHT (g) | CPQ (g) | BPO (g) | Monomer Blend (g) | Filler (g) |
|---|---|---|---|---|---|
| 12 | 0.123 | 0.438 | 1.094 | 175 | 205.4 |
| 13 | 0.049 | 0.10 | 0.5 | 40 | 47 |
| 14 | 0.059 | 0.10 | 0.5 | 40 | 47 |
| 15 | 0.069 | 0.10 | 0.485 | 40 | 47 |
| 16 | 0.048 | 0.10 | 0.485 | 40 | 47 |
| 17 | 0.048 | 0.10 | 0.515 | 40 | 47 |

TABLE 6

Examples with a combination of two amines

| Example | Sample | $T_{20}$ [sec] | $T_{80}$ [sec] | Delta T [sec] |
|---|---|---|---|---|
| 12 | A | 116 | 213 | 97 |
|  | B | 118 | 214 | 96 |
| 13 | A | 144 | 275 | 131 |
|  | B | 135 | 261 | 126 |
| 14 | A | 154 | 309 | 155 |
|  | B | 152 | 291 | 139 |
| 15 | A | 173 | 399 | 226 |
|  | B | 165 | 360 | 195 |
| 16 | A | 125 | 235 | 110 |
|  | B | 124 | 222 | 98 |
| 17 | A | 114 | 210 | 96 |
|  | B | 115 | 195 | 80 |

Examples 18–22

Base (reducing agent) paste for Example 18 was prepared by first dissovling 0.002 g BHT, 0.36 g Tinuvin P, 0.675 g DHEPT, and 0.191 g DMAPE in 43.9 g of a methacrylate monomer blend and stirring for two hours at 55° C. to 60° C. The monomer blend consisted of 11.41 g of a 90/10 by weight solution of Bis-GMA in TEGDMA, 4.09 g TEGDMA, 25.43 g UDMA, and 2.93 g Bis-EMA-6. To 40.09 g of this solution was first added 1.24 g of a 19.35 wt-% solution of PETMP in TEGDMA, and then 47 g of silane-treated $ZrO_2SiO_2$ filler. The composition was mechanically stirred for about 30 minutes at 100 rpm until a homogeneous paste was obtained.

Base (reducing agent) paste for Example 19 was made similarly by dissolving 0.0023 g BHT, 0.36 g Tinuvin P, 0.45 g DHEPT, and 0.381 g DMAPE in 43.87 g of a methacrylate monomer blend by mechanically stirring for two hours at 55° C. to 60° C. The monomer blend had the same composition as the one used for making the base paste of Example 18. To 40.06 g of this solution was first added 1.24 g of a PETMP solution (19.35 wt-% solution of PETMP in TEGDMA), and then 47 g of silane-treated $ZrO_2SiO_2$ filler. The composition was mechanically stirred for about 30 minutes at 100 rpm until a homogeneous paste was obtained.

The same oxidizing agent paste was used for both Examples 19 and 20, and was prepared by dissolving 0.14 g BHT, 0.5 g CPQ, and 1.25 g of BPO in a 200 g methacrylate monomer blend. The composition of the monomer blend was identical to that of the monomer blend described in Comparative Example 4C base paste. A clear solution was obtained after mechanically stirring for 4 hours at room temperature. Subsequently 234.8 g of a silane-treated $ZrO_2SiO_2$ filler was added to the resulting clear solution and mechanically stirred for 30 minutes at 100 rpm until a homogeneous paste was obtained.

Base (reducing agent) pastes for Examples 20 and 21 was prepared separately by first dissolving 0.002 g BHT, 0.36 g Tinuvin P, and appropriate amounts of DHEPT and DMAPE (0.338 g and 0.0953 g for Example 20; and 0.225 g and 0.191 g for Example 21) in 43.9 g of a methacrylate monomer blend by stirring for two hours at 55° C. to 60° C. The monomer blend for Examples 20 and 21 had the same composition as for the base pastes of Examples 18 and 19. To 39.7 g of this solution was first added 1.08 g of a PETMP solution (prepared by adding 0.44 g of PETMP to 5.50 g of TEGDMA), and then 47 g of silane-treated $ZrO_2SiO_2$ filler. The composition was mechanically stirred for about 30 minutes at 100 rpm until a homogeneous paste was obtained.

The same oxidizing agent paste was used for both Examples 20 and 21, and was prepared in the same way as reducing agent pastes for Examples 18 and 19. However, the amounts of BHT, CPQ and BPO dissolved in 200 g of monomer blend as prepared for Comparative Example 4C was 0.14 g, 0.5 g, and 2 g, respectively. Measurement of Shore A hardness for these materials to attain a reading of 20 and 80 as a function of time was collected for each of two samples.

TABLE 7

Examples with combination of a mercaptan with two amines

| Example | Sample | $T_{20}$ [sec] | $T_{80}$ [sec] | Delta T [sec] |
|---------|--------|----------------|----------------|---------------|
| 18 | A | 141 | 294 | 153 |
|    | B | 136 | 270 | 134 |
| 19 | A | 102 | 217 | 115 |
|    | B | 101 | 217 | 116 |
| 20 | A | 147 | 285 | 138 |
|    | B | 142 | 285 | 143 |
| 21 | A | 119 | 225 | 106 |
|    | B | 121 | 221 | 100 |

Examples 22–24

Base (reducing agent) pastes for Examples 22–24 were prepared separately by first dissolving 0.006 g BHT, 0.88 g Tinuvin P, and 1.1 g DHEPT in 110 g of a methacrylate monomer blend by stirring for two hours at 55° C. to 60° C. The composition of the monomer blend was identical to that of the monomer blend described in Comparative Example 4C base paste. Then, to 20.36 g of the resulting solution was first added an appropriate amount of a mercaptan, as listed in Table 8, and subsequently 23.5 g of silane-treated $ZrO_2SiO_2$ filler. The composition was mechanically stirred for about 30 minutes at 100 rpm until a homogeneous paste was obtained.

The same oxidizing agent paste was used for all three examples, which was prepared by dissolving 0.077 g BHT, 0.275 g CPQ, and 1.1 g of BPO in a 110 g methacrylate monomer blend. The composition of the monomer blend was identical to that of the monomer blend described in Comparative Example 4C base paste. A clear solution was obtained after mechanically stirring for 4 hours at room temperature. Subsequently, 129.1 g of a silane-treated $ZrO_2SiO_2$ filler was added to the resulting solution and mechanically stirred for 30 minutes at 100 rpm until a homogeneous paste was obtained. Measurement of Shore A hardness for these materials to attain a reading of 20 and 80 as a function of time was collected for each of two samples.

TABLE 8

Examples with combination of a mercaptan with an amines

| Example | Mercaptan (g) | Sample | $T_{20}$ [sec] | $T_{80}$ [sec] | Delta T [sec] |
|---------|---------------|--------|----------------|----------------|---------------|
| 22 | 0.4 | A | 152 | 272 | 120 |
|    | PETMP | B | 158 | 275 | 117 |
| 23 | 1.0 | A | 144 | 232 | 88 |
|    | PETMP | B | 138 | 230 | 92 |
| 24 | 0.67 | A | 125 | 217 | 92 |
|    | IOTG | B | 124 | 208 | 84 |

Amounts of mercaptan refer to grams of the different mercaptans in 20.36 g of the monomer blend of Comparative Example 4C containing BHT, Tinuvin P, and DHEPT.

Examples 25–27

Base (reducing agent) paste for Examples 25 was prepared by first dissolving 0.001 g BHT, 0.144 g Tinuvin P, 8.1 g DHEPT-di-IEM, and 0.157 g DMAPE in 18.0 g of a methacrylate monomer blend by stirring for two hours at 55° C. to 60° C. The monomer blend consisted of 5 g of a 90/10 by wt-% solution of Bis-GMA in TEGDMA, 0.4 g TEGDMA, 6.3 g UDMA, and 6.3 g Bis-EMA-6. To this solution was added 18 g of a silane-treated $ZrO_2SiO_2$ filler. The composition was mechanically stirred for about 30 minutes at 100 rpm until a homogeneous paste was obtained.

Oxidizing agent paste for Example 25 was prepared by dissolving 0.046 g BHT, 0.163 g CPQ, and 0.569 g of BPO in a 65 g methacrylate monomer blend. The monomer blend had the same composition as that used for preparing the oxidizing agent paste for Example 24 but without the mercaptan additive. A clear solution was obtained after mechanically stirring for 4 hours at room temperature. Subsequently 75 g of a silane-treated $ZrO_2SiO_2$ filler was added to it and mechanically stirred for 30 minutes at 100 rpm until a homogeneous paste was obtained.

Base (reducing agent) pastes for Examples 26 and 27 were prepared separately by first dissolving 0.12 g Tinuvin P, 6.75 g DHEPT-di-IEM, and an appropriate amount of DMAPE (0.06 g for Example 26, and 0.023 g for Example 27) in 15 g of a methacrylate monomer blend by stirring for two hours at 55° C. to 60° C. The composition of the monomer blend was identical to that of the monomer blend described in Comparative Example 4C base paste. To this solution was added 15 g of silane-treated $ZrO_2SiO_2$ filler. The composition was mechanically blended for about 30 minutes until a homogeneous paste was obtained.

The same oxidizing agent paste was used for both Examples 26 and 27, which was prepared by dissolving 0.110 g BHT, 0.188 g CPQ, and 0.938 g of BPO in a 75 g methacrylate monomer blend. The composition of the monomer blend was identical to that of Comparative Example 4C base paste. A clear solution was obtained after mechanically stirring for 4 hours at room temperature. Subsequently, 234.78 g of silane-treated $ZrO_2SiO_2$ filler was added to the resulting clear solution and mechanically stirred for 30 minutes at 100 rpm until a homogeneous paste was obtained. Measurement of Shore A hardness for these materials to attain a reading of 20 and 80 as a function of time was collected for each of two samples.

TABLE 9

Examples with a non-polymerizable and a polymerizable amine

| Example | Sample | $T_{20}$ [sec] | $T_{80}$ [sec] | Delta T [sec] |
|---|---|---|---|---|
| 25 | A | 100 | 225 | 125 |
|  | B | 98 | 214 | 116 |
| 26 | A | 121 | 236 | 115 |
|  | B | 119 | 233 | 114 |
| 27 | A | 157 | 324 | 167 |
|  | B | 154 | 325 | 171 |

Examples 28 and 29

The same base (reducing agent) paste was used for both Examples 28 and 29. The paste was prepared by dissolving 0.3 g Tinuvin P, and 18 g DHEPT-di-IEM in 40.0 g of a methacrylate monomer blend by stirring for two hours at 55° C. to 60° C. The composition of the monomer blend was identical to that of the monomer blend described in Comparative Example 4C. To this solution was added 40 g of silane-treated $ZrO_2SiO_2$ filler. The composition was mechanically stirred for about 30 minutes at 100 rpm until a homogeneous paste was obtained.

Oxidizing agent pastes for Examples 28 and 29 were prepared separately by dissolving 0.05 g CPQ, 1.5 g of BPO, and either 0.029 g BHT (for Example 28) or 0.022 g BHT (for Example 29) in a 20 g methacrylate monomer blend. The composition of the monomer blend was identical to that of the monomer blend described in Comparative Example 4C. A clear solution was obtained after mechanically stirring for 4 hours at room temperature. Subsequently, 20 g of a silane treated $ZrO_2SiO_2$ filler was added to it each solution and mechanically blended until a homogeneous paste was obtained. Measurement of Shore A hardness for these materials to attain a reading of 20 and 80 as a function of time was collected for each of two samples.

TABLE 10

Examples containing a polymerizable amine

| Example | Sample | $T_{20}$ [sec] | $T_{80}$ [sec] | Delta T [sec] |
|---|---|---|---|---|
| 28 | A | 160 | 334 | 174 |
|  | B | 163 | 320 | 157 |
| 29 | A | 135 | 258 | 123 |
|  | B | 140 | 251 | 111 |

Examples 30 and 31

Base (reducing agent) paste for Example 30 was made by preparing a first solution of 0.225 g CPQ, 0.72 g Tinuvin-P, and 1.881 g DHEPT in a 90 g methacrylate monomer blend; and a second solution of 0.125 g CPQ, 0.4 g Tinuvin-P, and 0.886 g DMAPE in a 50 g methacrylate monomer blend. Both monomer blends had the same composition, which is identical to that of the monomer blend described in Comparative Example 4C. Clear solutions were obtained after mechanically stirring for two hours at 55° C. to 60° C. Then 21.92 g of the first solution and 3.86 g of the second solution were combined, and to the combined solution was added 25 g of silane-treated quartz filler. This paste was mechanically stirred for 30 minutes at 100 rpm until a homogeneous paste was obtained.

Base (reducing agent) paste for Example 31 was prepared similarly, except that 1.494 g DHEPT was used in the first solution and 0.703 g DMAPE in the second. Moreover, 21.82 g of the first solution was blended with 3.84 g of the second solution, and to this resulting solution was added 25.0 g of silane treated quartz filler. This paste was mechanically stirred for 30 minutes at 100 rpm until a homogeneous paste was obtained.

Oxidizing agent pastes for both Examples 30 and 31 were identical in formulation but were prepared separately. Briefly, 1.25 g of BPO and 0.25 g BHT were dissolved in 100 g of a methacrylate monomer blend by stirring for four hours at room temperature. The composition of the monomer blend was identical to that of the monomer blend described in Comparative Example 4C. Subsequently, 100 g of silane-treated quartz filler was added to it each solution and mechanically stirred for 30 minutes at 100 rpm until a homogeneous paste was obtained. Measurement of Shore A hardness for these materials to attain a reading of 20 and 80 as a function of time was collected for each of two samples.

TABLE 11

Examples containing two amines and silane treated quartz filler

| Example | Sample | $T_{20}$ [sec] | $T_{80}$ [sec] | Delta T [sec] |
|---|---|---|---|---|
| 30 | A | 141 | 274 | 133 |
|  | B | 137 | 274 | 137 |
| 31 | A | 157 | 303 | 146 |
|  | B | 158 | 296 | 138 |

TABLE 12

Properties of some selected examples after light cure

| Example | CS [MPa] | DTS [MPa] | Barcol Hardness Top | Barcol Hardness Bottom |
|---|---|---|---|---|
| 12 | 407.4 | 66.90 | 54 | 49 |
| 13 | 397.5 | 58.55 | 57 | 51 |
| 26 | 409.9 | 55.08 | 57 | 51 |
| 27 | 392.6 | 52.66 | 48 | 50 |
| 28 | 388.6 | 55.81 | 53 | 54 |
| 29 | 362.3 | 44.48 | 61 | 58 |

CS and DTS values are the average of 5 samples, while Barcol hardness values are the average of 3 readings per sample.

Example 32

Base (reducing agent) paste for Example 32 was made by preparing a solution of 0.063 g CPQ, 0.2 g Tinuvin-P, 0.392 g DHEPT, 0.111 g DMAPE in a 25 g methacrylate monomer blend. The monomer blend consisted of 6.37 g of a 90/10 by wt-% solution of Bis-GMA in TEGDMA, 12.18 g UDMA, 5.73 g Bis-EMA-6, and 0.52 g TEGDMA. A clear solution was obtained after mechanically stirring for two hours at 55° C. to 60° C. To this solution was added 0.52 g of Tween-40, 0.75 g Cab-O-Sil M-5, and 20 g of silane-treated quartz filler. This paste was mechanically stirred for 30 minutes at 100 rpm until a homogeneous paste was obtained.

Oxidizing agent paste for Example 32 was prepared by dissolving 0.3125 g of BPO and 0.063 g BHT in 25 g of a methacrylate monomer blend by stirring for four hours at room temperature. The composition of the monomer blend was identical to that of the monomer blend described in Example 32 base paste. Subsequently, 0.52 g of Tween-40, 0.75 g Cab-O-Sil M-5, and 20 g of silane-treated quartz filler was added to it. This paste was mechanically stirred for 30 minutes at 100 rpm until a homogeneous paste was obtained.

Measurement of Shore A hardness for these materials to attain a reading of 20 and 80 as a function of time was collected for each of two samples.

TABLE 13

Examples containing two amines, Tween-40, pyrogenic silica, and silane treated quartz filler

| Example | Sample | $T_{20}$ [sec] | $T_{80}$ [sec] | Delta T [sec] |
|---------|--------|----------------|----------------|---------------|
| 32 | A | 145 | 290 | 145 |
|  | B | 140 | 268 | 128 |

Example 33

Base (reducing agent) paste for Example 33 was made by preparing a solution of 0.0468 g BHT, 2.4 g Tinuvin-P, 6.0 g DHEPT, and 1.2711 g DMAPE in a 300 g methacrylate monomer blend. The monomer blend consisted of 76.4 g of a 90/10 by wt-% solution of Bis-GMA in TEGDMA, 146.13 g UDMA, 68.79 g Bis-EMA-6, and 8.7 g TEGDMA. A clear solution was obtained after mechanically stirring for two hours at 55° C. to 60° C. To 129.1 g of this solution was added 3.75 g Aerosil R-972, and 146.3 g of silane-treated quartz filler. This paste was mechanically blended in a double planetary mixer (Charles Ross & Son Company, Hauppauge, N.Y.) for 20 minutes at 20 rpm, thereby obtaining a homogeneous paste.

Oxidizing agent paste for Example 33 was prepared by dissolving 0.8906 g of BHT, 0.225 g of CPQ, and 3.75 g of BPO in 300 g of a methacrylate monomer blend by stirring for four hours at room temperature. The composition of the monomer blend was identical to that of the monomer blend described in Example 33 base paste. To 127.1 g of the monomer blend was added 7.5 g of Tween-40, 7.5 g Cab-O-Sil M-5, and 100 g of silane-treated quartz filler. This paste was mechanically blended in a double planetary mixer for 20 minutes at 20 rpm, thereby obtaining a homogeneous paste. Measurement of Shore A hardness for these materials to attain a reading of 20 and 80 as a function of time was collected for each of two samples.

TABLE 14

Examples containing two amines, Tween-40, pyrogenic silica, and silane treated quartz filler

| Example | Sample | $T_{20}$ [sec] | $T_{80}$ [sec] | Delta T [sec] |
|---------|--------|----------------|----------------|---------------|
| 33 | A | 122 | 296 | 174 |
|  | B | 104 | 285 | 181 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claim is set forth herein as follows.

What is claimed is:

1. A dental material comprising:
   a hardenable resin system; and
   a first initiator system capable of hardening the hardenable resin; wherein the first initiator system comprises at least one oxidizing agent and at least one tertiary aromatic amine reducing agent and at least one mercaptan reducing agent;
   wherein the hardenable resin system and the first initiator system are selected such that when combined the resultant composition has an initial set phase time of less than about 180 seconds at room temperature, and an extended flexible phase working time of greater than about 85 seconds at room temperature; and
   a second initiator system.

2. A dental material comprising:
   a hardenable resin system; and
   a first initiator system capable of hardening the hardenable resin; wherein the first initiator system comprises at least one oxidizing agent and at least two mercaptan reducing agents;
   wherein the hardenable resin system and the first initiator system are selected such that when combined the resultant composition has an initial set phase time of less than about 180 seconds at room temperature, and an extended flexible phase working time of greater than about 85 seconds at room temperature.

3. A dental material comprising:
   a hardenable resin system; and
   a first initiator system capable of hardening the hardenable resin; wherein the first initiator system comprises at least one oxidizing agent and at least one tertiary aromatic amine reducing agent and at least one mereaptan reducing agent;
   wherein the hardenable resin system and the first initiator system are selected such that when combined the resultant composition has an initial set phase time of less than about 180 seconds at room temperature, and an extended flexible phase working time of greater than about 85 seconds at room temperature; and
   wherein at least one of the tertiary aromatic amine reducing agents is a polymerizable tertiary aromatic amine.

4. A dental material comprising;
   a hardenable resin system; and
   a first initiator system capable of hardening the hardenable resin; wherein the first initiator system comprises at least one oxidizing agent and at least one reducing agent, wherein the reducing agent is a polymerizable tertiary aromatic amine; wherein the polymerizable tertiary aromatic amine is selected from the group consisting of bis-N,N-[2-(2-methacryloloxyethylaminocarbonyloxy)ethyl]-p-toluidine, bis-N,N-(2-methacryloloxyethyl)-p-toluidine, 4-[2(2-acrylamido-2-methylpropionyloxy)ethyl)-N,N-dimethlyaniline, bis-N,N-[2-(2-acrylamido-2-methylpropionyloxy)ethyl]-p-toluidine, and mixtures thereof;
   wherein the hardenable resin system and the first initiator system are selected such that when combined the resultant composition has an initial set phase time of less than about 180 seconds at room temperature, and an extended flexible phase working time of greater than about 85 seconds al room temperature.

5. A dental material comprising:
   a hardenable resin system; and
   a first initiator system capable of hardening the hardenable resin; wherein the first initiator system comprises at least one oxidizing agent and at least one tertiary aromatic amine reducing agent and at least one mercaptan reducing agent;

wherein the hardenable resin system and the first initiator system are selected such that when combined the resultant composition has an initial set phase time of less than about 180 seconds at room temperature, and an extended flexible phase working time of greater than about 85 seconds at room temperature;

wherein the hardenable resin system comprises at least one ethylenically unsaturated compound; and wherein at least one of the tertiary aromatic amine reducing agents is a polymerizable tertiary aromatic amine.

6. A dental restorative prepared from a dental material comprising:

a hardenable resin system; and a first initiator system capable of hardening the hardenable resin; wherein the first initiator system comprises, at least one oxidizing agent and at least one tertiary aromatic amine reducing agent and at least one mercaptan reducing agent;

wherein the hardenable resin system and the first initiator system are selected such that when combined the resultant composition has an initial set phase time of less than about 180 seconds at room temperature, and an extended flexible phase working time of greater than about 85 seconds at room temperature.

7. The dental restorative of claim 6 selected from the group consisting of an inlay, onlay, veneer, crown, and bridge.

8. The dental restorative of claim 6 which is a provisional restorative.

9. The dental restorative of claim 8 wherein the provisional restorative is a temporary crown or a temporary bridge.

10. A dental material which is in at least two parts, comprising:

a hardenable resin system; and a first initiator system capable of hardening the hardenable resin; wherein the first initiator system comprises at least one oxidizing agent and at least one tertiary aromatic amine reducing agent and at least one mercaptan reducing agent;

wherein the hardenable resin system and the first initiator system are selected such that when combined the resultant composition has an initial set phase time of less than about 180 seconds at room temperature, and an extended flexible phase working time of greater than about 85 seconds at room temperature;

wherein at least one part includes the at least two reducing agents and at least one part includes at least one oxidizing agent, which together form the first initiator system; and wherein at least one part includes at least one initiator of a second initiator system.

11. The dental material of claim 10 wherein the initiator is a photinitiator.

12. The dental material of claim 11 wherein the photinitiator is camphorquinone.

13. A dental material comprising a hardenable resin system and a first initiator system capable of hardening the hardenable resin, wherein the first initiator system comprises at least one polymerizable tertiary aromatic amine; wherein the polymerizable tertiary aromatic amine is selected from the group consisting of bis-N,N-[2-(2-methacryloloxyethylaminocarbonyloxy)ethyl]-p-toluidine, bis-N,N-(2-methacryloloxyethyl)-p-toluidine, 4-[2(2-acrylamido-2-methylpropionyloxy)ethyl)-N,N-dimethlyaniline bis-N,N-[2-(2-acrylamido-2-methylpropionyloxy)ethyl]-p-toluidine, and mixtures thereof.

14. A dental material comprising:

a hardenable resin system; and a first initiator system capable of hardening the hardenable resin; wherein the first initiator system comprises at least two peroxide oxidizing agents and at least one tertiary aromatic amine reducing agent and at least one mercaptan reducing agent;

wherein the hardenable resin system and the first initiator system are selected such that when combined the resultant composition has an initial set phase time of less than about 180 seconds at room temperature, and an extended flexible phase working time of greater than about 85 seconds at room temperature.

15. A kit for preparation of a dental restorative, the kit comprising:

a first container comprising at least one tertiary aromatic amine reducing agent and at least one mercaptan reducing agent;

a second container comprising at least one oxidizing agent;

at least a portion of a hardenable resin system in at least one of the containers;

wherein the hardenable resin system, reducing agent, and oxidizing agent are selected such that when combined the resultant composition has an initial set phase time of less than about 180 seconds at room temperature, and an extended flexible phase working time of greater than about 85 seconds at room temperature;

at least one filler in each of the containers; and at least one initiator of a second initiator system in at least one of the containers.

16. The kit of claim 15 wherein the initiator is a photoinitiator.

17. A kit for preparation of a dental restorative, the kit comprising:

a first container comprising at least two mercaptan reducing agents;

a second container comprising at least one oxidizing agent; and at least a portion of a hardenable resin system in at least one of the containers;

wherein the hardenable resin system, reducing agent, and oxidizing agent are selected such that when combined the resultant composition has an initial set phase time of less than about 180 seconds at room temperature, and an extended flexible phase working time of greater than about 85 seconds at room temperature.

18. A kit for preparation of a dental restorative, the kit comprising:

a first container comprising at least one tertiary aromatic amine reducing agent and at least one mercaptan reducing agent;

a second container comprising at least one oxidizing agent; and at least a portion of a hardenable resin system in at least one of the containers;

wherein the hardenable resin system, reducing agent, and oxidizing agent are selected such that when combined the resultant composition has an initial set phase time of less than about 180 seconds at room temperature, and an extended flexible phase working time of greater than about 85 seconds at room temperature; and wherein at least one of the tertiary aromatic amine reducing agents is a polymerizable tertiary aromatic amine reducing agents.

19. A kit for preparation of a dental restorative, the kit comprising:
a first container comprising at least one polymerizable tertiary aromatic amine reducing agent; wherein the polymerizable tertiary aromatic amine is selected from the group consisting of bis-N,N-[2-(2-methacryloloxyethylaminocarbonyloxy)ethyl]-p-toluidine, bis-N,N-(2-methacryloloxyethyl)-p-toluidine, 4-[2(2-acrylamido-2-methylpropionyloxy)ethyl]-N,N-dimethylaniline bis-N,N-[2-(2-acrylamido-2-methylpropionyloxy)ethyl]-p-toluidine, and mixtures thereof;
a second container comprising at least one oxidizing agent; and
at least a portion of a hardenable resin system in at least one of the containers;
wherein the hardenable resin system, reducing agent and oxidizing agent are selected such that when combined the resultant composition has an initial set phase time of less than about 180 seconds a room temperature, and an extended flexible phase working time of greater than about 85 seconds at room temperature.

20. A kit for preparation of a dental restorative, the kit comprising:
a first container comprising at least one oxidizing agent;
a second container comprising at least one polymerizable tertiary aromatic amine reducing agent; wherein the polymerizable tertiary aromatic amine is selected from the group consisting of bis-N,N-[2-(2-methacryloloxyethylaminocarbonyloxy)ethyl]-p-toluidine, bis-N,N-(2-methacryloloxyethyl)-p-toluidine, 4-[2(2-acrylamido-2-methylpropionyloxy)ethyl]-N,N-dimethlyaniline, bis-N,N-[2-(2-acrylamido-2-methylpropionyloxy)ethyl]-p-toluidine, and mixtures thereof; and
a hardenable resin system in at least one of the containers.

21. A method for preparing a dental restorative, the method comprising:
making an impression of at least one tooth;
filling the impression with a hardenable composition comprising a hardenable resin system and a first initiator system; wherein the first initiator system comprises at least one polymerizable tertiary aromatic amine, wherein the polymerizable tertiary aromatic amine is selected from the group consisting of bis-N,N-[2-2-methacryloloxyethylaminocarbonyloxy)ethyl]-p-toluidine, bis-N,N-(2-methacryloloxyethyl)-p-toluidine, 4-[2(2-acrylamido-2-methylpropionyloxy)ethyl]-N,N-dimethlyaniline, bis-N,N-[2-(2-acrylamido-2-methylpropionyloxy)ethyl]-p-toluidine, and mixtures thereof;
wherein the hardenable resin system and the first initiator system are selected such that when combined the resultant composition has an initial set phase time of less than about 180 seconds at room temperature, and an extended flexible phase working time of greater than about 85 seconds at room temperature;
placing the impression over at least one tooth for a sufficient time to partially harden the hardenable composition;
removing the impression and partially hardened composition and removing excess hardened material to form a dental restorative; and
allowing the dental restorative to further harden.

22. A method for preparing a dental restorative, the method comprising:
making an impression of at least one tooth;
filling the impression with a hardenable composition comprising a hardenable resin system and a first initiator system; wherein the first initiator system comprises at least one oxidizing agent and at least one tertiary aromatic amine reducing agent and at least one mercaptan reducing agent;
wherein the hardenable resin system and the first initiator system are selected such that when combined the resultant composition has an initial set phase time of less than about 180 seconds at room temperature, and an extended flexible phase working time of greater than about 85 seconds at room temperature;
placing the impression over at least one toot for a sufficient time to partially harden the hardenable composition;
removing the impression and partially hardened composition and removing excess hardened material to form a dental restorative; and
allowing the dental restorative to further harden.

23. The method of claim 22 wherein the oxidizing agent is a peroxide compound.

24. The method of claim 22 wherein the dental material further comprises a second initiator system.

25. The method of claim 22 wherein at least one of the tertiary aromatic amine reducing agents is a polymerizable tertiary aromatic amine.

26. The method of claim 22 wherein at least one of the tertiary aromatic amine reducing agents is a tertiary aromatic airline of the formula:

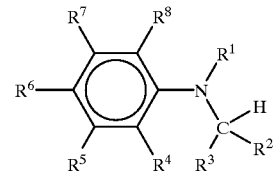

wherein each R group is independently H or an organic group that does not adversely effect the initiation of hardening of the dental material.

27. A method for preparing a dental restorative, the method comprising:
making an impression of at least one tooth;
filling the impression with a hardenable composition comprising a hardenable resin system and a first initiator system; wherein the first initiator system comprises at least one oxidizing agent and at least two mercaptan reducing agents;
wherein the hardenable resin system and the first initiator system are selected such that when combined the resultant composition has an initial set phase time of less than about 180 seconds at room temperature, and an extended flexible phase working time of greater than about 85 seconds at room temperature;
placing the impression over at least one tooth for a sufficient time to partially harden the hardenable composition;
removing the impression and partially hardened composition and removing excess hardened material to form a dental restorative; and
allowing the dental restorative to further harden.

* * * * *

UNITED STATES PATENT AND TRADEMARK OFFICE
CERTIFICATE OF CORRECTION

PATENT NO.    : 6,624,211 B2
DATED         : September 23, 2003
INVENTOR(S)   : Karim, Naimul It is certified that error appears in the above-identified patent and that said Letters Patent is hereby corrected as shown below:

Title page,
Item [56], References Cited, OTHER PUBLICATIONS,
"Kirk—Othmer" reference, delete "11, 19-23," and insert -- 11, 13, 19-23 --.

Column 2,
Line 15, delete "acrylic bur" and insert -- acrylic burr --.

Column 3,
Line 7, delete "methacryloloxyethylaminocarbonyloxy)" and insert
-- methacryloyloxyethylaminocarbonyloxy --.
Line 8, delete "(2-methacryloloxyethyl)" and insert -- (2-methacryloyloxyethyl) --.
Line 10, delete "dimethlyaniline" and insert -- dimethylaniline --.

Column 4,
Lines 34-35, delete "or multiple unit bridges. "Provisional" and insert
-- or multiple unit bridges.
        Provisional --. (Begin new paragraph.).

Column 8,
Line 54, delete "(2-methacryloloxyethyl" and insert -- (2-methacryloyloxyethyl --.
Line 57, delete "dimethlyaniline" and insert -- dimethylaniline --.
Line 59, delete "(2-methacryloloxyethyl)" and insert -- (2-methacryloyloxyethyl) --.
Line 67, delete "isooctylthioglycoate" and insert -- issoctylthioglycolate --.

Column 9,
Line 1, delete "iogylcoate" and insert -- ioglycolate --.

Column 10,
Line 33, delete "mn" and insert -- nm --.
Line 45-46, delete "Cl , Br , I , or $C_4H_5SO_3$ )" and insert -- $Cl^-$, $Br^-$, $I^-$, or $C_4H_5,SO_3^-$ ) --.
Line 47, delete "$SbF_5OH$ or $AsF_6$ )" and insert -- $SbF_5OH^-$ or $AsF_6^-$ ) --.

Column 11,
Line 42, delete "$(R^{11})_4$" and insert -- $(R^{11})_{4-}$ --.

Column 15,
Line 66, delete "homogenous" and insert -- homogeneous --.

Column 17,
Line 50, delete "systems" and insert -- Systems --.

UNITED STATES PATENT AND TRADEMARK OFFICE
CERTIFICATE OF CORRECTION

PATENT NO. : 6,624,211 B2
DATED : September 23, 2003
INVENTOR(S) : Karim, Naimul It is certified that error appears in the above-identified patent and that said Letters Patent is hereby corrected as shown below:

Column 18,
Line 20, delete "cartridges" and insert -- cartridge --.
Line 47, delete "monomer blend of described" and insert -- monomer blend as described --.

Column 19,
Line 26, delete "blend of described" and insert -- blend as described --.

Column 20
Line 10, delete "cartridges" and insert -- cartridge --.
Line 44, delete "Examples 18-22" and insert -- Examples 18-21 --.
Line 46, delete "dissovling" and insert -- dissolving --.

Column 22,
Line 11, delete "mercaptan with an amines" and insert -- mercaptan with an amine --.
Line 26, delete "Examples 25" and insert -- Example 25 --.

Column 23,
Line 36, delete "added to it each solution" and insert -- added to each solution --.

Column 24,
Line 16, delete "added to it each solution" and insert -- added to each solution --.

Column 25,
Line 62, delete "claim is set forth" and insert -- claims set forth --.

Column 26,
Line 39, delete "dental material comprising;" and insert -- dental material comprising: --.
Line 49, delete "methacryloloxyethyl" and insert -- methacryloyloxyethyl --.
Line 50, delete "(2-methacryloloxyethyl)" and insert -- (2-methacryloyloxyethyl) --.
Line 52, delete "dimethlyaniline" and insert -- dimethylaniline --.
Line 60, delete "85 seconds al" and insert -- 85 seconds at --.

Column 27,
Line 16, delete "comprises," and insert -- comprises --.
Line 56, delete "photinitiator" and insert -- photoinitiator --.
Lines 57-58, delete "photinitiator" and insert -- photoinitiator --.
Line 65, delete "methacryloloxyethyl" and insert -- methacryloyloxyethyl --.
Line 66, delete "(2-methacryloloxyethyl)" and insert -- (2-methacryloyloxyethyl) --.

UNITED STATES PATENT AND TRADEMARK OFFICE
CERTIFICATE OF CORRECTION

PATENT NO. : 6,624,211 B2
DATED : September 23, 2003
INVENTOR(S) : Karim, Naimul It is certified that error appears in the above-identified patent and that said Letters Patent is hereby corrected as shown below:

Column 28,
Line 1, delete "dimethlyaniline" and insert -- dimethylaniline --.

Column 29,
Line 3, delete "agents" and insert -- agent --.
Line 10, delete "methacryloloxyethyl" and insert -- methacryloyloxyethyl --.
Line 11, delete "(2-methacryloloxyethyl)" and insert -- (2-methacryloyloxyethyl) --.
Line 13, delete "dimethlyaniline bis" and insert -- dimethylaniline, bis --.
Line 22, delete "seconds a room" and insert -- seconds at room --.
Line 32, delete "methacryloloxyethyl" and insert -- methacryloyloxyethyl --.
Line 33, delete "(2-methacryloloxyethyl)" and insert -- (2-methacryloyloxyethyl) --.
Line 35, delete "dimethlyaniline" and insert -- dimethylaniline --.
Line 49, delete "methacryloloxyethyl" and insert -- methacryloyloxyethyl --.
Line 50, delete "(2-methacryloloxyethyl)" and insert -- (2-methacryloyloxyethyl) --.
Line 52, delete "dimethlyaniline" and insert -- dimethylaniline --.

Column 30,
Line 16, delete "toot" and insert -- tooth --.
Line 32, delete "airline" and insert -- amine --.

Signed and Sealed this

Thirtieth Day of May, 2006

JON W. DUDAS
*Director of the United States Patent and Trademark Office*